United States Patent [19]
Bidwell et al.

[11] Patent Number: 5,779,670
[45] Date of Patent: Jul. 14, 1998

[54] CATHETER HAVING LUBRICATED SHEATHING

[76] Inventors: Robert E. Bidwell, 27 Montrose Pl., Melville, N.Y. 11747; Arnold Melman, 23 Agnes Cir., Ardsley, N.Y. 10502

[21] Appl. No.: 455,126

[22] Filed: May 31, 1995

[51] Int. Cl.$^6$ .................................................. A61M 5/00
[52] U.S. Cl. ........................ 604/172; 604/265; 604/271; 604/96
[58] Field of Search .................. 604/96, 103, 108, 604/158, 163, 171, 172, 264, 265, 54, 280, 282, 271; 606/108

[56] References Cited

U.S. PATENT DOCUMENTS

| | | |
|---|---|---|
| 3,053,257 | 9/1962 | Birtwell . |
| 3,168,092 | 2/1965 | Silverman ................. 128/1.2 |
| 3,169,527 | 2/1965 | Sheridan . |
| 3,500,819 | 3/1970 | Silverman ................. 128/1.2 |
| 3,583,391 | 6/1971 | Cox et al. ................. 128/2 |
| 3,589,356 | 6/1971 | Silverman ................. 128/1.2 |
| 3,669,099 | 6/1972 | Silverman ................. 128/2 M |
| 3,683,928 | 8/1972 | Kuntz . |
| 3,726,281 | 4/1973 | Norton et al. . |
| 3,853,130 | 12/1974 | Sheridan . |
| 4,271,839 | 6/1981 | Fogarty et al. ................. 128/344 |
| 4,318,947 | 3/1982 | Joung . |
| 4,539,234 | 9/1985 | Sakamoto et al. . |
| 4,606,347 | 8/1986 | Fogarty et al. ................. 128/344 |
| 4,686,124 | 8/1987 | Onohara et al. . |
| 4,810,543 | 3/1989 | Gould et al. . |
| 4,863,440 | 9/1989 | Chin ................. 604/271 |
| 4,976,703 | 12/1990 | Franetzki et al. . |
| 5,013,306 | 5/1991 | Solomon et al. . |
| 5,013,717 | 5/1991 | Solomon et al. . |
| 5,026,607 | 6/1991 | Kiezulas . |
| 5,098,379 | 3/1992 | Conway et al. . |
| 5,171,305 | 12/1992 | Schickling et al. ................. 604/271 |
| 5,178,611 | 1/1993 | Rosenberg . |
| 5,179,174 | 1/1993 | Elton . |
| 5,209,726 | 5/1993 | Goosen . |
| 5,266,359 | 11/1993 | Spielvogel . |
| 5,269,755 | 12/1993 | Bodicky . |
| 5,269,770 | 12/1993 | Conway et al. . |
| 5,300,032 | 4/1994 | Hibbs et al. . |
| 5,331,027 | 7/1994 | Whitbourne . |

FOREIGN PATENT DOCUMENTS

| | | |
|---|---|---|
| 0227583 | 7/1987 | European Pat. Off. . |
| 0247559 | 12/1987 | European Pat. Off. . |
| WO 91/10466 | 7/1991 | WIPO . |

Primary Examiner—Corrine M. McDermott
Assistant Examiner—Cris L. Rodriguez
Attorney, Agent, or Firm—Dilworth & Barrese

[57] ABSTRACT

A urethral catheter assembly is disclosed which includes an elongate catheter body having an expandable retention balloon provided at a distal end thereof, and a progressively deployable lubricated sheath which encloses the exterior surface of the catheter body. Once deployed, the sheath permits relative movement of the catheter body relative to the urethra without causing discomfort or trauma to the patient.

20 Claims, 8 Drawing Sheets

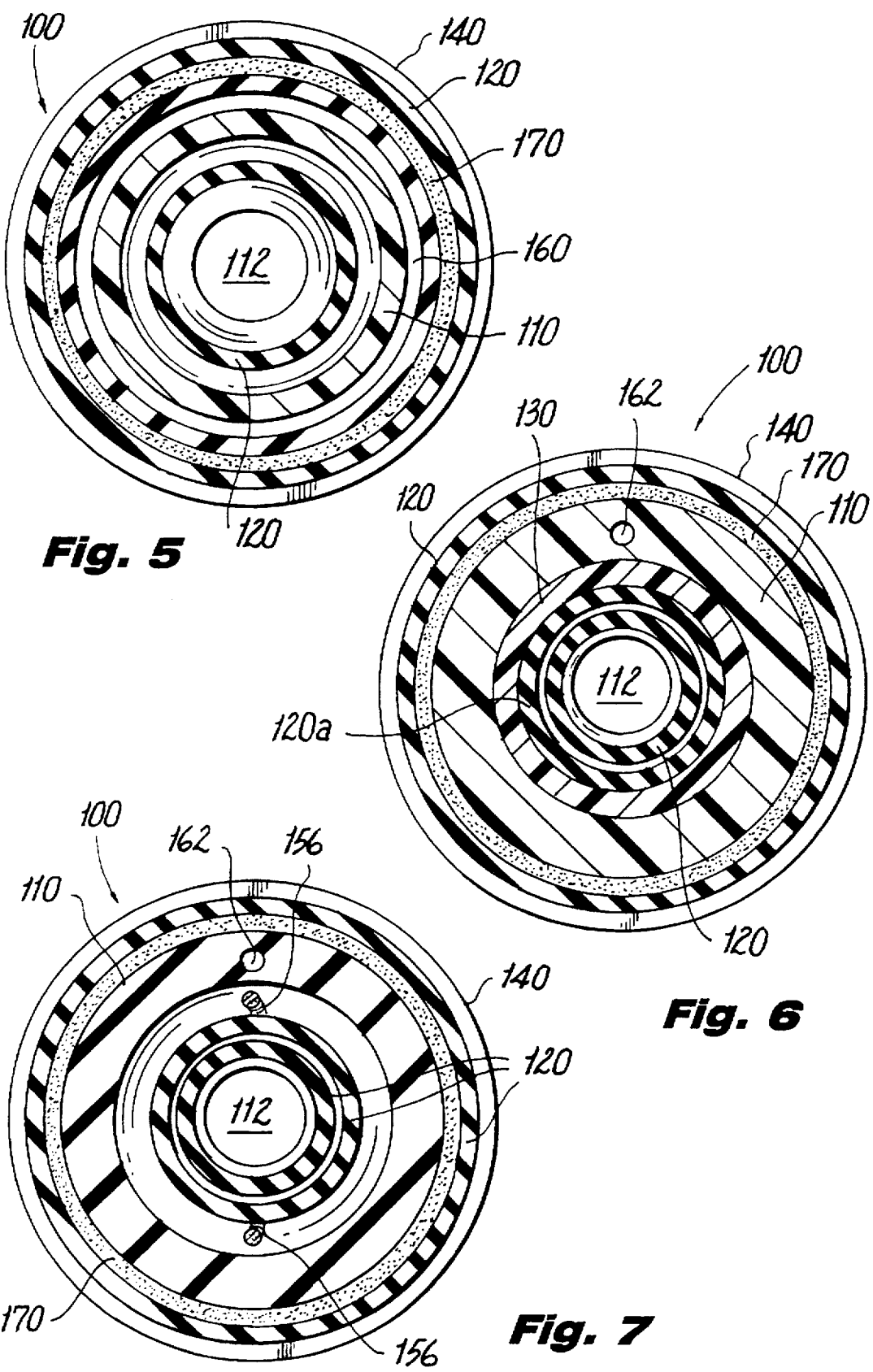

CATHETER HAVING LUBRICATED SHEATHING

BACKGROUND OF THE INVENTION

1. Field of the Invention

The subject invention is directed to catheters, and more particularly, to a urinary catheter having a sheath with a sealed lubricant between the sheath and the drain to reduce irritation to the urethra during insertion and removal of the catheter, and while the catheter is positioned therein.

2. Description of the Related Art

Urethral catheters that are placed within a patient's lower urinary tract are well known in the art. One type of urethral catheter is a retention catheter. Retention catheters are supported in the patient's bladder to continuously remove urine therefrom. One type of urinary retention catheter is known in the art as a Foley catheter. It consists of an elongated tube through which extends a main drain lumen. The catheter is placed through the patient's urethra so that the distal end thereof extends into the patient's bladder and the proximal end remains outside the patient's body. An inlet opening is provided at the distal end of the catheter to allow urine to drain into the main lumen and pass into a collection bag associated with the proximal end of the catheter.

Foley catheters are retained within the patient's bladder and urethra by an inflatable balloon located at the distal end of the elongated tube proximate to the inlet opening of the main lumen. An inflation lumen connects the balloon to the proximal end of the catheter so that a liquid may be passed under pressure to the balloon to expand the balloon. A valve is generally provided to maintain the liquid under pressure so that the balloon remains inflated.

Often, a urinary catheter will remain within the urethra for weeks at a time, presenting general discomfort to the patient. Such discomfort will be heightened when there is relative movement between the catheter and the urethra. This discomfort results from friction between the outer wall of the catheter and the inner wall of the urethra, and is magnified by even minimal movement of the patient. In addition, the internal cardiac rhythm of the body creates an irritating friction generating movement of the urethra relative to the catheter. This irritation may be compounded by infection, further complicating and lengthening patient recovery. Even greater discomfort will be experienced when the catheter is removed from the urethra after use.

Several prior art devices have been provided to reduce such discomfort through the use of lubricants, as described, for example, in U.S. Pat. Nos. 3,726,281 and 5,098,379. In U.S. Pat. No. 5,209,726, a catheter is disclosed which has an elongated body enclosed by a resilient sleeve which defines a cavity containing a lubricating substance effective to permit the sleeve to slide along the outer surface of the catheter body. Thus, in use, when the catheter body moves in response to movements of the patient's body, the sleeve will not move relative to the urethra. However, during insertion and removal of this catheter, significant frictional contact will occur between the sleeve and the urethra, causing considerable discomfort to the patient. The subject invention provides an improvement over these prior art devices.

SUMMARY

The subject invention is directed to a urethral catheter assembly configured to reduce patient discomfort during insertion, utilization and removal. The catheter assembly includes an elongate catheter body having an interior lumen extending therethrough defined by an interior surface, and an elongated tubular sheath which is operatively associated with the catheter body and which encloses the exterior surface thereof. A first end of the tubular sheath is supported adjacent the interior surface of the catheter body and a second end is supported adjacent the exterior surface of the catheter body. A layer of lubricant is disposed between the tubular sheath and the catheter body along the respective interior and exterior surfaces thereof to reduce frictional resistance between the sheath and the catheter body and promote relative movement therebetween during utilization.

In a preferred embodiment of the subject invention, a substantial portion of the lubricated sheath is disposed within the interior lumen of the catheter body prior to insertion of the catheter assembly into the urethra. In use, the lubricated sheath is progressively deployed from the interior lumen of the catheter body as the catheter assembly is inserted into the urethra to continuously enclose the exterior surface of the catheter body and provide a buffer between the catheter body and the urethral wall. Upon becoming fully deployed, the lubricated sheath permits movement of the catheter body relative to the urethral wall without causing trauma thereto, thus reducing patient discomfort.

Preferably, the first end of the lubricated sheath is retained by a sled that is disposed within the interior lumen of the catheter body, and upon withdrawing the catheter assembly from the urethra, the sled is moved through the interior lumen to draw the lubricated sheath thereinto. Preferred embodiments of the subject catheter assembly also include a radially expandable anchoring mechanism, in the form of a balloon, which is operatively associated with the exterior surface of the catheter body adjacent the distal end thereof for retaining the catheter assembly in a patient's bladder. Means extend through the catheter body to direct a fluid to the anchoring mechanism.

Further features of the subject invention will become more readily apparent from the following detailed description of the invention taken in conjunction with accompanying drawings.

BRIEF DESCRIPTION OF THE DRAWINGS

Preferred embodiments of the catheter assembly of the subject invention as well as prior art catheters will be described hereinbelow with reference to the drawings, wherein:

FIG. 5 is a cross-sectional view of the catheter assembly taken along line 4—4 of FIG. 4;

FIG. 6 is a cross-sectional view taken along line 6—6 of FIG. 4;

FIG. 7 is a cross-sectional view taken along line 7—7 of FIG. 4;

DETAILED DESCRIPTION OF THE PREFERRED EMBODIMENTS

Figure 2:
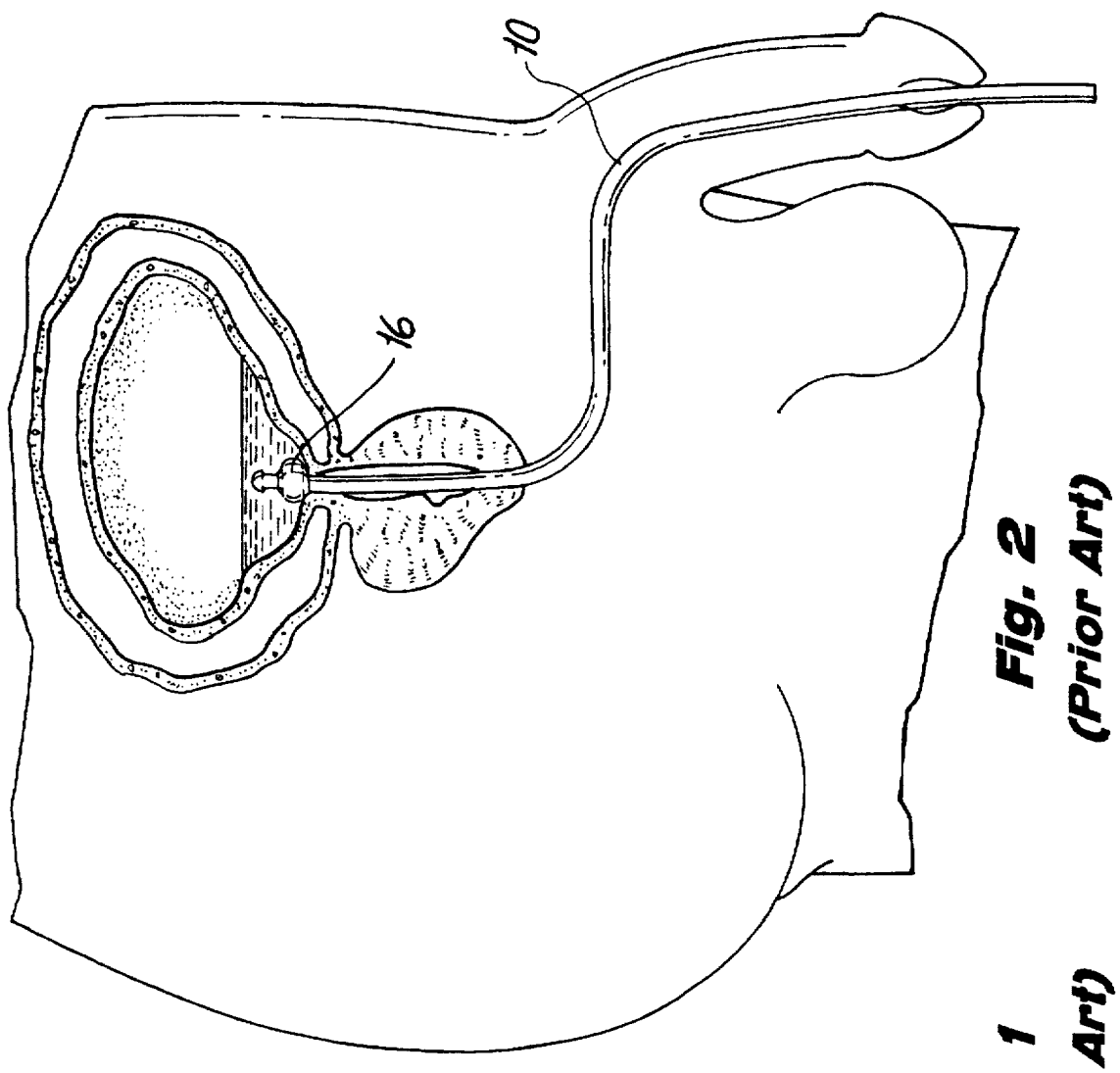
FIG. 2 illustrates the prior art Foley catheter of FIG. 1 extended through a patient's urethra and retained within their bladder.

In the drawings and in the description which follows, the term "proximal", as is traditional, will refer to the end of the surgical apparatus which is closest to the operator, while the term "distal" will refer to the end which is furthest from the operator.

Figure 1:
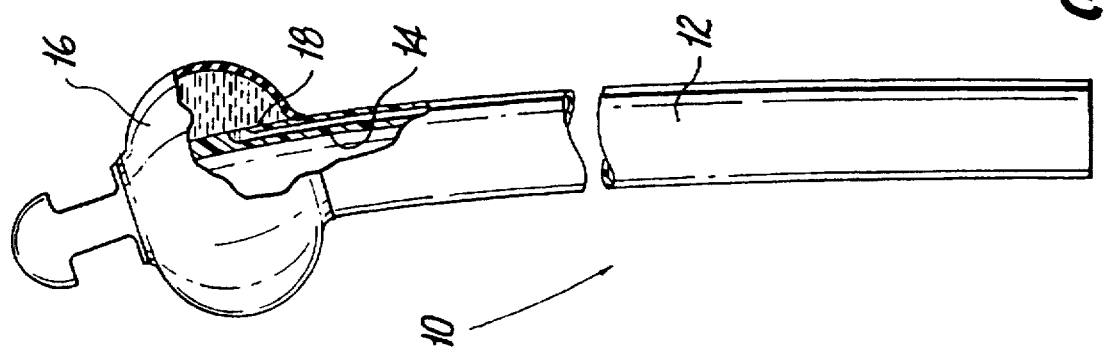
FIG. 1 is an elevational view of a prior art Foley catheter with a distal portion thereof broken away to illustrate an interior portion of the expandable balloon anchor associated therewith.

Referring now to the drawings, there is illustrated in FIG. 1 a prior art Foley catheter 10 having an elongated body 12 through which extends an interior lumen 14. An expandable balloon 16 is provided adjacent the distal end of body 12 for retaining catheter 10 within a patient's bladder, as illustrated in FIG. 2. A passage 18, shown in FIG. 1, extends through catheter body 12 for delivering pressurized fluid to the expandable balloon 16 to facilitate the expansion thereof.

Once the prior art Foley catheter 10 has been positioned in the patient's urethra, and retained within the bladder, it serves to drain urine from the bladder to a collection bag adjacent the proximal end of the catheter. Because the exterior surface of the catheter body remains in contact with the interior surface of the urethra at all times, movement of the prior art catheter, while emplaced, as well as during insertion and removal thereof, can cause significant trauma and/or discomfort to the patient. The subject catheter assembly, which is illustrated in FIG. 3, is intended to reduce such discomfort by providing a lubricated buffering structure between the exterior surface of the catheter body and the interior surface of the urethra so that when the catheter body moves, it does not directly effect the urethra, i.e. there is no frictional contact therebetween.

Figure 3:
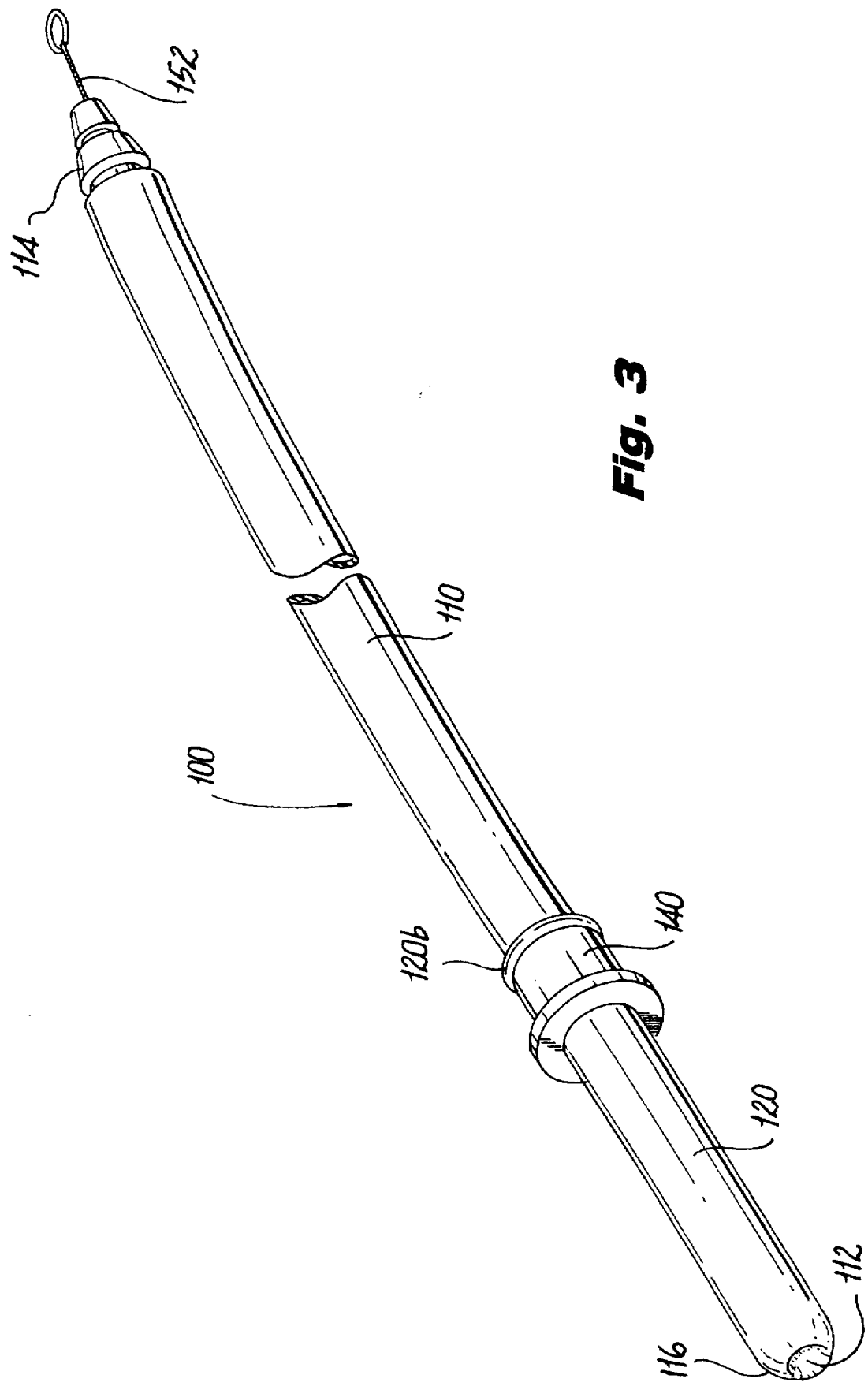
FIG. 3 is a perspective view of a urethral catheter assembly constructed in accordance with a preferred embodiment of the subject invention.

Referring now to FIG. 3, a catheter assembly constructed in accordance with a preferred embodiment of the subject invention is illustrated and is designated generally by reference numeral 100. Catheter assembly 100 includes an elongate catheter body 110 having an interior lumen 112 extending therethrough between proximal and distal ends 114 and 116 thereof. A connective fitting is defined at the proximal end 116 of catheter body 110 for attachment of a drainage bag (not shown). An expandable lubricated sheath 120, having a tubular configuration and formed of a resilient material such as latex, is operatively associated with catheter body 110. One end 120a (See FIG. 4) of lubricated sheath 120 is supported within the interior lumen 112 and the opposed end 120b is supported adjacent the exterior surface of catheter body 110.

Figure 4:
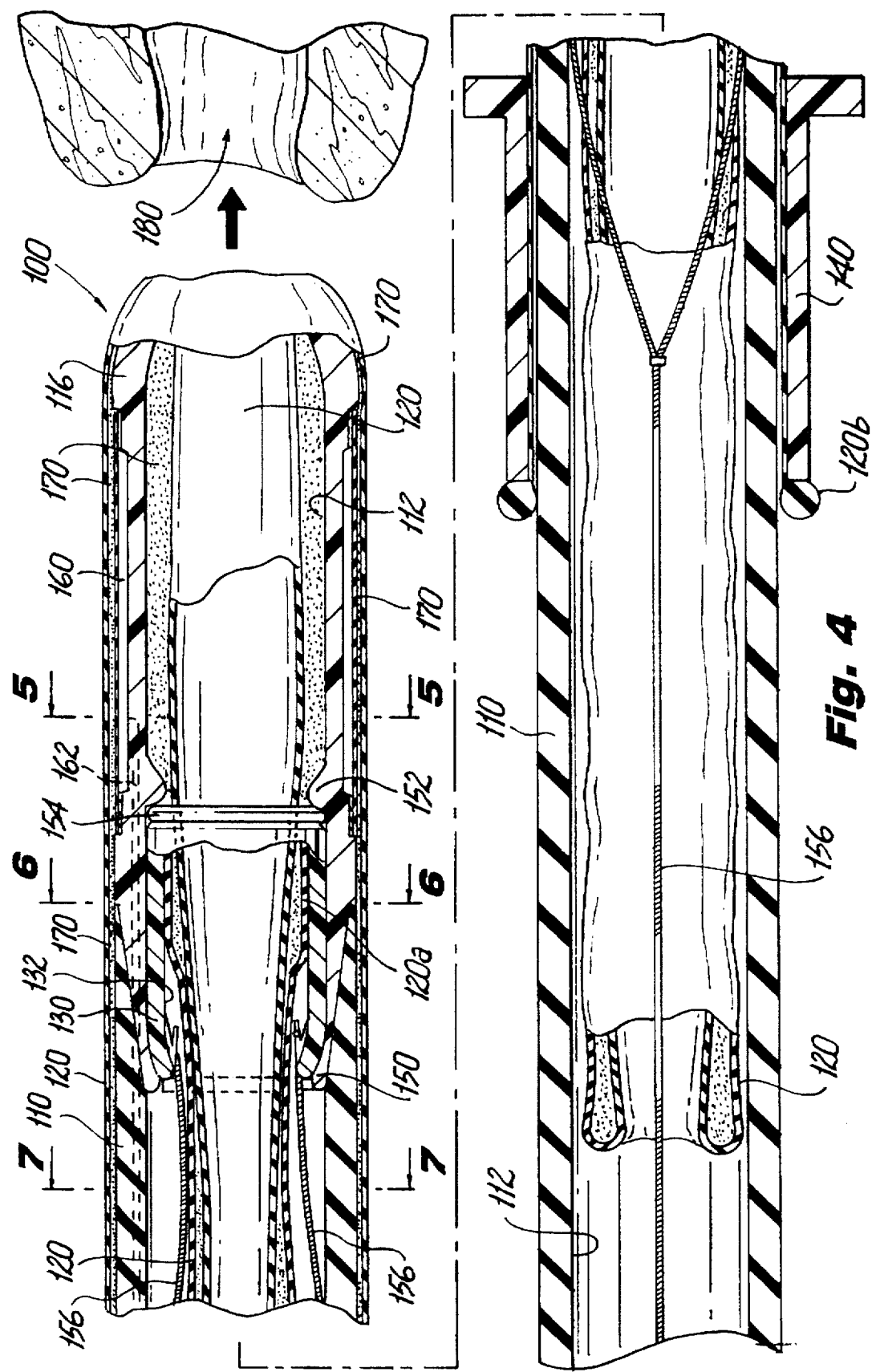
FIG. 4 is a side elevational view in cross-section of the urethral catheter assembly of FIG. 3 prior to its insertion into the urethra of a patient.

More particularly, as best seen in FIG. 4, the interior end 120a of sheath 120 is mounted to a retention sled 130 disposed within the interior lumen 112 of catheter body 110, and the exterior end 120b of sheath 120 is mounted at a location proximate anchor collar 140. The majority of sheath 120 (i.e. a substantial portion of its length) is initially maintained within the interior lumen 112 and is preferably stored therein until catheter assembly 100 is inserted into a patient's urethra. In addition to supporting the interior end 120a of sheath 120, retention sled 130 also serves to withdraw the sheath into the interior lumen 112 of catheter body 110 as catheter assembly 100 is withdrawn from the patient's urethra. Flanged anchor collar 140, in addition to supporting the exterior end 120b of sheath 120, provides the surgeon with a support structure to grasp and manipulate the catheter body during insertion and removal of the catheter assembly.

Referring to FIG. 4, in its pre-operative condition, retention sled 130 is maintained in an immobile position within the interior lumen 112 of the catheter body 110 by a plurality of spaced apart radially inwardly biased securement tabs 150 which frictionally engage the outer periphery of the sled 130. An abutment flange 152 formed within the interior lumen of the catheter body 110 limits distal movement of sled 130, and an annular sealing ring 154 is positioned adjacent abutment flange 152 to prevent leakage through the securement tabs. Retention sled 130 has an axial bore 132 extending therethrough which accommodates passage of the lubricated sheath 120. Moreover, axial bore 132 enables sheath 120 to extend twice therethrough. Once, extending in a proximal direction, and a second time, extending in a distal direction, everted within itself, extending from the distal end 116 of interior lumen 112, and enclosing the exterior surface of catheter body 110. This pre-operative condition of the sheath is best illustrated in FIGS. 5–7, wherein FIG. 5 illustrates two layers of sheath 120 proximal to the sled, FIG. 6 illustrates two layers of the sheath within the axial bore of the sled, and FIG. 7 illustrates a single layer of the sheath extending distally from the sled. A looped drawstring 156 is anchored within axial bore 132 and extends from a proximal end of retention sled 130, through interior lumen 112, to the proximal end 114 of catheter body 110. Drawstring 156 facilitates axial movement of sled 130 within lumen 112 when catheter assembly 100 is removed from the urethra.

As best seen in FIG. 4, an expandable plenum 160 is formed in catheter body 110 adjacent the distal end 116 thereof. A conduit 162 is defined in catheter body 110 for directing pressurized fluid into the expandable plenum. The plenum, when expanded, defines a retention balloon which anchors the distal portion of the catheter assembly 100 within the patient's bladder, as illustrated in FIG. 9.

Referring now to FIGS. 8–11, there is illustrated in sequential order, the steps of insertion, stabilization, and removal of catheter assembly 100. Initially, as illustrated in FIG. 4, prior to inserting catheter assembly 100 in the patient's urethra, indicated by reference numeral 180, retention sled 130 is engaged by securement tabs 150 and is maintained in an immobile position adjacent the distal end 116 of catheter body 110. At such a time, a majority of the lubricated sheath 120 is disposed within the interior lumen 112 of catheter body 110 in an everted condition.

Figure 8:
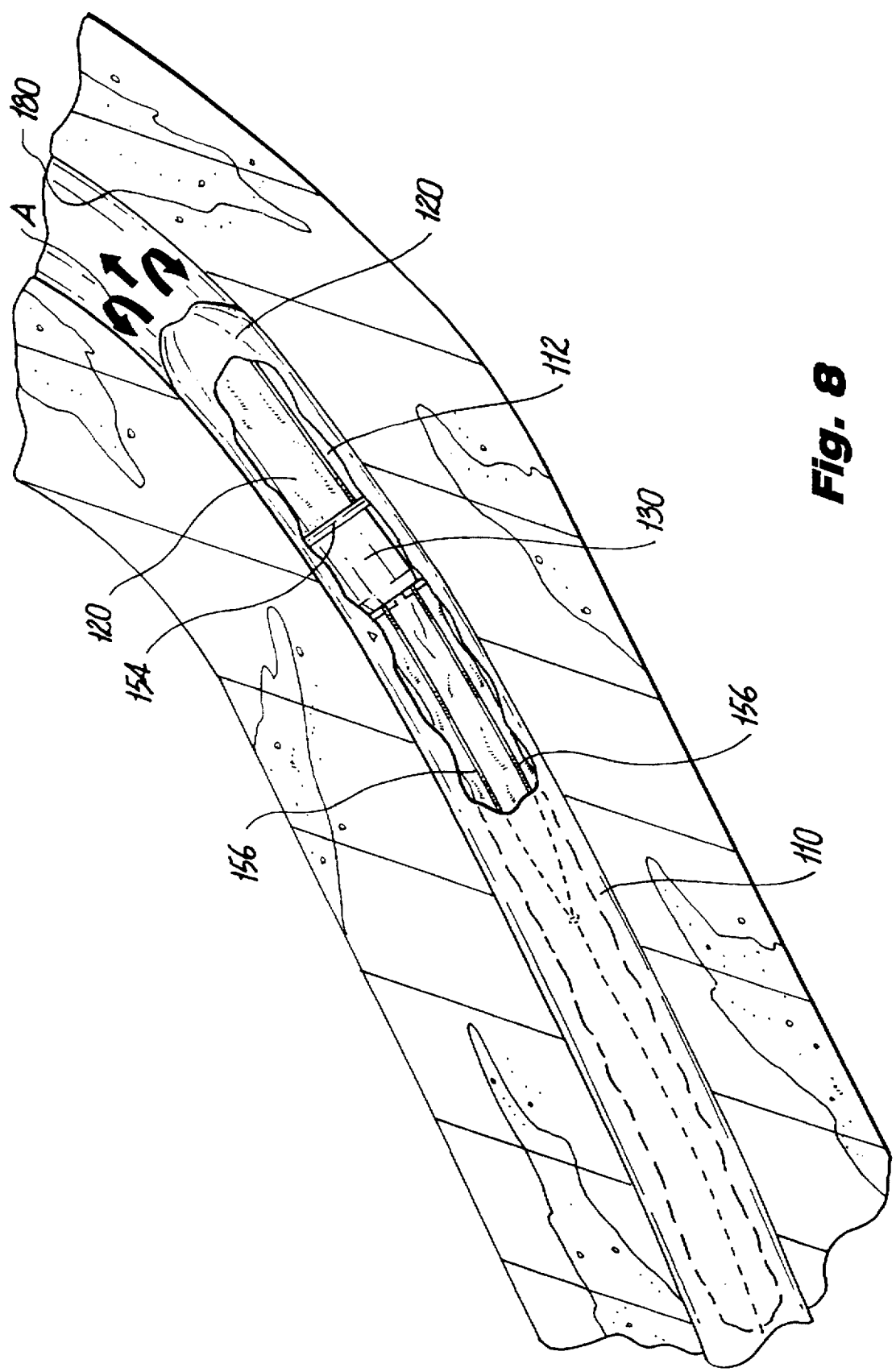
FIG. 8 illustrates the progressive insertion of the urethral catheter assembly of FIG. 3 into the urethra of a patient with the lubricated sheath deploying from the interior lumen of the catheter body to enclose the exterior surface thereof.

Turning now to FIG. 8, as catheter assembly 100 is inserted through the urethra 180 of the patient, lubricated sheath 120 is progressively deployed from interior lumen 112, as indicated by the directional arrows designated "A". During such a deployment, there is no frictional contact between the exterior surface of catheter body 110 and the interior of the urethra. As a result, no trauma is caused to the urethral wall and little discomfort is felt by the patient. Continued insertion of catheter assembly 100 causes progressive deployment of lubricated sheath 120 until the distal end portion of catheter assembly 100 extends into the patient's bladder.

Figure 9:
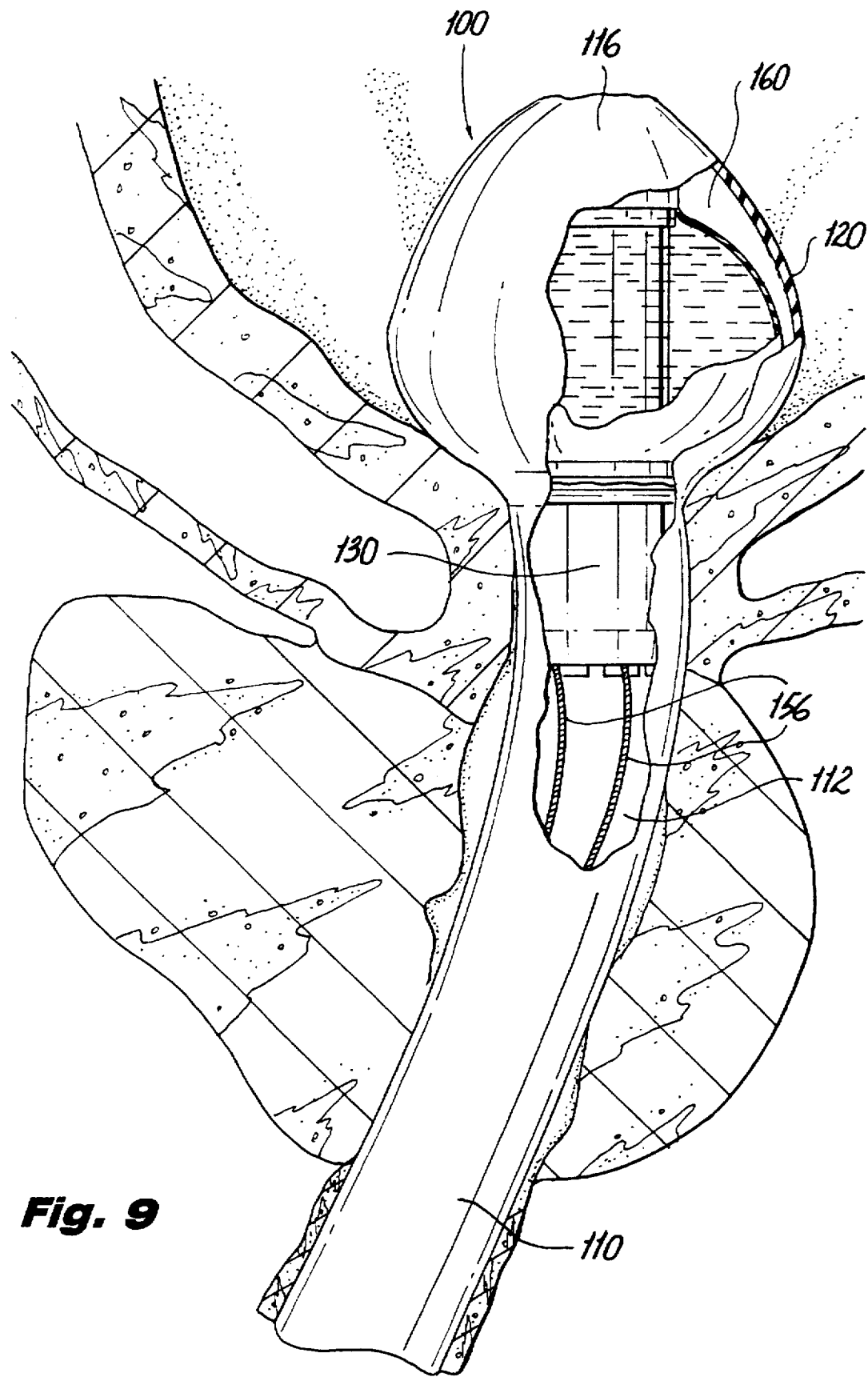
FIG. 9 illustrates the distal portion of the catheter assembly of FIG. 3 in a deployed position anchored within the patient's bladder.

At such a time, as illustrated in FIG. 9, pressurized fluid is transferred into the expandable plenum 160 through conduit 162 and the balloon anchor is formed to stabilize and maintain the distal portion of catheter assembly 100 within the bladder. Once located therein, catheter assembly 100 serves as a drain to advantageously remove urine from the bladder through interior lumen 112. When catheter assembly 100 is deployed in such a manner, the lubricated sheath 120 acts as a buffering structure between the exterior surface of catheter body 110 and the interior wall of the urethra 180. Thus, relative movement between the catheter body and the urethra will not cause pain or discomfort to the patient. Those skilled in the art will readily appreciate that this relative movement will be enhanced by the presence of the lubrication on the sheath. Preferably, the lubrication consists of a gel-type lubricant, i.e. a bio-compatible petroleum based lubricant. Layers of lubricant are best seen in FIGS. 5–7, and designated by reference numeral 170.

Figure 10:
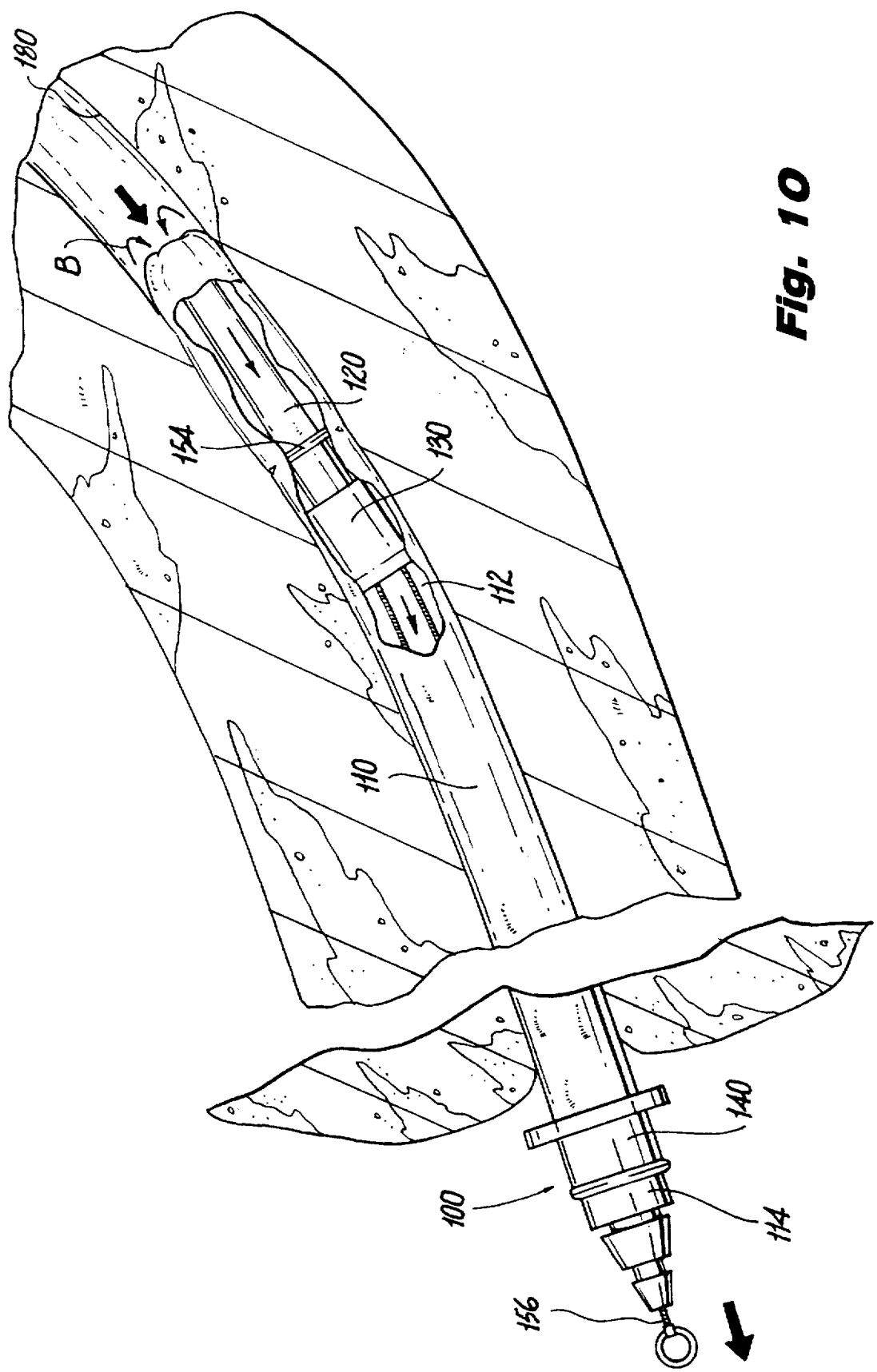
FIG. 10 illustrates the progressive removal of the catheter assembly from the patient's urethra as the lubricated sheath is drawn into the interior lumen of the catheter body.

Prior to removal of catheter assembly 100 from the patient's urethra, plenum 160 is drained and the anchor balloon is reduced to its normal diameter equal to that of catheter body 110. Then, as illustrated in FIG. 10, to remove catheter assembly 100 from urethra 180, drawstring 156 is pulled proximally, releasing retention sled 130 from securement tabs 152 and enabling proximal movement thereof. Thereafter, as sled 130 is pulled through interior lumen 112, the sheath 120 is drawn into the lumen, as indicated by the directional arrows designated "B". As a result, catheter body 110 is progressively urged in a proximal direction through the urethra.

Figure 11:
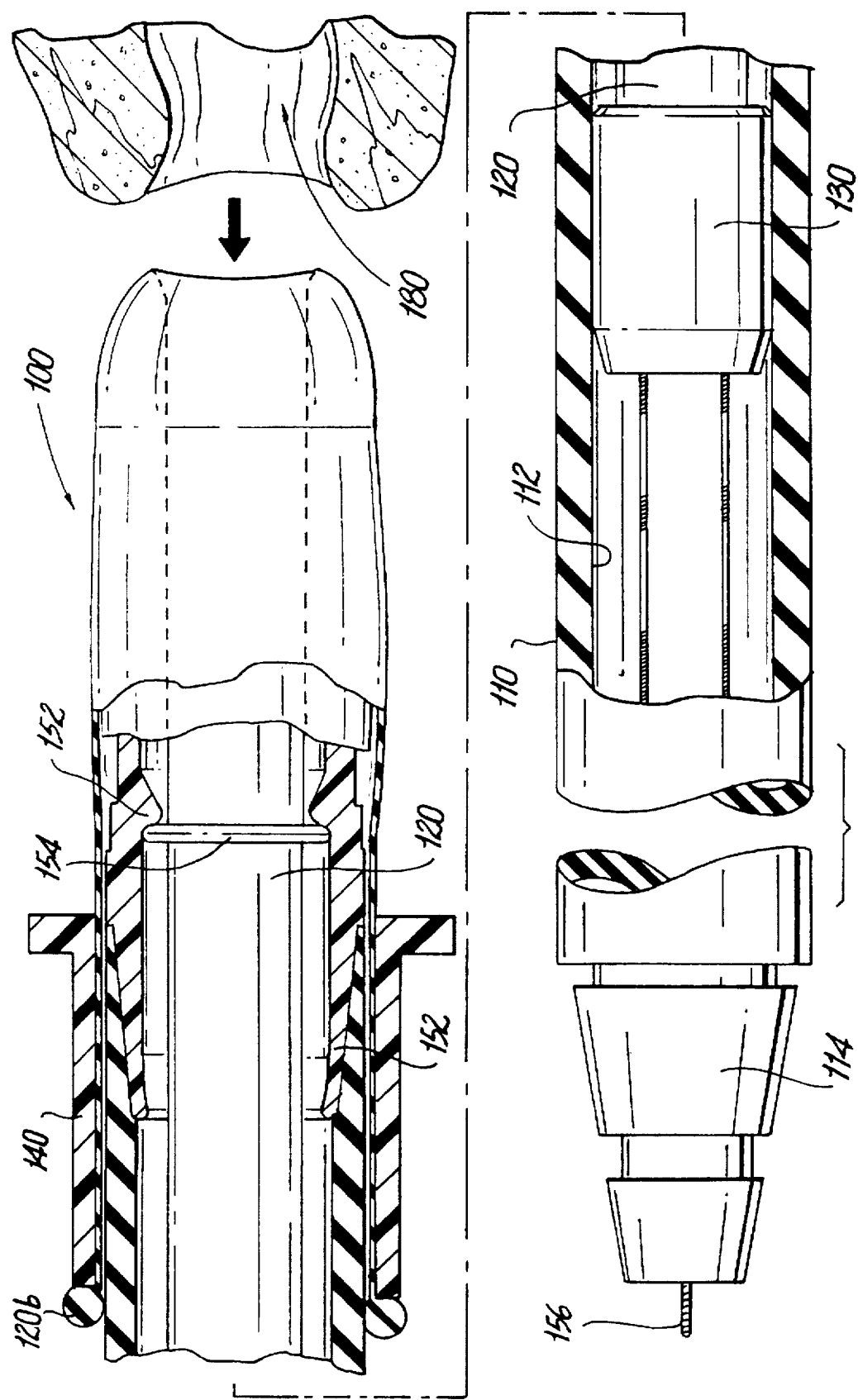
FIG. 11 is a side elevational view in cross-section of the catheter assembly of FIG. 3 after it has been removed from the patient's urethra and the lubricated sheath is fully withdrawn into the interior lumen of the catheter body.

During removal, there is no frictional contact between the exterior surface of the catheter body and the inner wall of the urethra, thus no discomfort is experienced by the patient. As illustrated in FIG. 11, when catheter assembly 100 is fully removed from the urethra, retention sled 130 is disposed adjacent the proximal end 114 of catheter body 110 along with the interior end 120a of sheath 120. At such a time, the entire catheter assembly may be discarded.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

We claim:

1. A catheter assembly which comprises:
   (a) an elongate catheter body having a proximal and a distal end, said catheter body having an interior lumen extending therethrough defined by an interior surface and having an exterior surface;
   (b) an elongate tubular sheath operatively associated with said catheter body and having opposed first and second ends, the first end of said sheath sealingly attached adjacent the interior surface of said catheter body and the second end of said sheath sealingly attached adjacent the exterior surface of said catheter body; and
   (c) a layer of lubricant sealingly disposed between said sheath and said catheter body along the interior and exterior surfaces thereof to reduce frictional resistance between said sheath and said catheter body, the tubular sheath being positioned at least partially about the catheter body such that the layer of lubricant is disposed between the interior surface of the tubular sheath and the exterior surface of the catheter body to permit relative movement therebetween.

2. A catheter assembly as recited in claim 1, further comprising a retention sled disposed within the interior lumen of said catheter body and configured to retain the first end of said sheath.

3. A catheter assembly as recited in claim 2, wherein said retention sled is mounted for axial movement within the interior lumen of said catheter body.

4. A catheter assembly as recited in claim 3, further comprising means extending through said interior lumen from the proximal end of said catheter body for effectuating axial movement of said retention sled.

5. A catheter assembly as recited in claim 4, wherein said means for effectuating axial movement of said retention sled comprises an elongated drawstring.

6. A catheter assembly as recited in claim 3, further comprising means associated with the interior lumen of said catheter body for releasably maintaining said retention sled in an immobilized position adjacent the distal end of said catheter body.

7. A catheter assembly as recited in claim 1, further comprising a radially expandable anchoring mechanism operatively associated with the exterior surface of said catheter body adjacent the distal end thereof.

8. A catheter assembly as recited in claim 1, further comprising means extending through said catheter body for directing a pressurized fluid to said radially expandable anchoring mechanism.

9. A catheter assembly as recited in claim 1, further comprising an annular griping collar positioned adjacent the distal end of said catheter body for supporting the second end of said sheath.

10. A urethral catheter assembly which comprises:
    (a) an elongate catheter body having a proximal and a distal end, said catheter body having an interior lumen extending therethrough defined by an interior surface and having an exterior surface; and
    (b) an elongate lubricated tubular sheath operatively associated with said catheter body and having opposed first and second ends, the first end of said lubricated sheath sealingly attached adjacent the interior surface of said catheter body and the second end of said lubricated sheath sealingly attached adjacent the exterior surface of said catheter body, a substantial portion of said lubricated sheath disposed within the interior lumen of said catheter body prior to insertion of the catheter assembly into the urethra, whereby the lubricated sheath is progressively deployed from the interior lumen of the catheter body as the catheter assembly is inserted into the urethra, to continuously enclose the exterior surface of the catheter body, the lubricated sheath having lubricant positioned between the exterior surface of the catheter body and the interior surface of the lubricated sheath, such that upon becoming fully deployed, the lubricated sheath permits movement of the catheter body relative to the urethra and the lubricated tubular sheath without causing trauma thereto.

11. A urethral catheter assembly as recited in claim 10, further comprising a retention sled disposed within the interior lumen of said catheter body and configured to retain the first end of said sheath, said retention sled mounted for axial movement within the interior lumen of said catheter body.

12. A urethral catheter assembly as recited in claim 11, wherein an elongated drawstring extends from said retention sled, through the interior lumen of said catheter body, to the proximal end thereof for effectuating axial movement of said retention sled in a proximal direction to withdraw the lubricated sheath into the interior lumen of said catheter body as the catheter assembly is removed from the urethra.

13. A urethral catheter assembly as recited in claim 10, further comprising a plurality of spaced apart radially inwardly extending tabs disposed within the interior lumen of said catheter body adjacent the distal end thereof for releasably maintaining said retention sled in an immobilized position.

14. A urethral catheter assembly as recited in claim 10, further comprising a radially expandable balloon operatively associated with the exterior surface of said catheter body adjacent the distal end thereof.

15. A urethral catheter assembly as recited in claim 14, further comprising means extending through said catheter body from the proximal end thereof for directing a pressurized fluid to said radially expandable balloon.

16. A urethral catheter assembly as recited in claim 10, further comprising an annular griping collar positioned adjacent the distal end of said catheter body and configured to maintain the second end of said lubricated sheath adjacent the exterior surface of said catheter body.

17. A urethral catheter assembly which comprises:

(a) an elongate catheter body having a proximal and a distal end, said catheter body having an interior lumen extending therethrough defined by an interior surface and having an exterior surface;

(b) a retention sled disposed within the interior lumen of said catheter body and mounted for axial movement therein; and (c) an elongate lubricated sheath operatively associated with said catheter body and having opposed first and second ends, the first end of said lubricated sheath sealingly attached to said retention sled adjacent the interior surface of said catheter body and the second end of said lubricated sheath sealingly attached adjacent the exterior surface of said catheter body, a substantial portion of said lubricated sheath disposed within the interior lumen of said catheter body prior to insertion of the catheter assembly into the urethra, whereby the lubricated sheath is progressively deployed from the interior lumen of the catheter body as the catheter assembly is inserted into the urethra, to continuously enclose the exterior surface of the catheter body, the lubricated sheath having lubricant positioned between the exterior surface of the catheter body and the interior surface of the lubricated sheath, such that upon becoming fully deployed, the lubricated sheath permits movement of the catheter body relative to the urethra and the lubricated tubular sheath without causing trauma thereto, and upon withdrawing said catheter assembly from the urethra, said retention sled moving through said interior lumen to withdraw the lubricated sheath thereinto.

18. A urethral catheter assembly as recited in claim 17, wherein an elongated drawstring extends from said retention sled, through the interior lumen of said catheter body, to the proximal end thereof for effectuating axial movement of said retention sled in a proximal direction to withdraw the lubricated sheath into the interior lumen of said catheter body as the catheter assembly is removed from the urethra.

19. A urethral catheter assembly as recited in claim 17, further comprising an annular griping collar positioned adjacent the distal end of said catheter body and configured to maintain the second end of said lubricated sheath adjacent the exterior surface of said catheter body.

20. A urethral catheter assembly as recited in claim 17, further comprising a radially expandable balloon operatively associated with the exterior surface of said catheter body adjacent the distal end thereof.

* * * * *